(12) United States Patent
Jiang et al.

(10) Patent No.: US 12,702,652 B2
(45) Date of Patent: Aug. 11, 2026

(54) BHB LIPOSOMES AND PREPARATION METHODS THEREOF

(71) Applicant: NANJING NUTRABUILDING BIO-TECH CO., LTD., Nanjing (CN)

(72) Inventors: Long Jiang, Nanjing (CN); Xuyang Sun, Nanjing (CN); Qiru Fan, Nanjing (CN); Ronghua Yi, Nanjing (CN); Mingru Wang, Nanjing (CN); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 271 days.

(21) Appl. No.: 18/363,531

(22) Filed: Aug. 1, 2023

(65) Prior Publication Data

US 2023/0404952 A1 Dec. 21, 2023

Related U.S. Application Data

(63) Continuation of application No. PCT/CN2022/075372, filed on Feb. 7, 2022.

(30) Foreign Application Priority Data

Feb. 2, 2021 (WO) ................ PCT/CN2021/074773

(51) Int. Cl.

*A61K 31/19* (2006.01)
*A61K 9/127* (2025.01)

(Continued)

(52) U.S. Cl.

CPC .............. *A61K 31/19* (2013.01); *A61K 9/127* (2013.01); *A61K 9/1277* (2013.01); *A61K 47/24* (2013.01); *A61P 3/00* (2018.01)

(58) Field of Classification Search

CPC ...... A61K 31/19; A61K 9/127; A61K 9/1277; A61K 9/1271

See application file for complete search history.

(56) References Cited

U.S. PATENT DOCUMENTS

| | | | | |
|---|---|---|---|---|
| 5,512,295 A * | 4/1996 | Kornberg | ........... | A61K 47/6911 264/4.1 |
| 5,585,249 A | 12/1996 | Reusch | | |

(Continued)

FOREIGN PATENT DOCUMENTS

| | | | |
|---|---|---|---|
| CN | 107802508 A | 3/2018 | |
| CN | 111534561 A | 8/2020 | |
| WO | WO-02096458 A1 * | 12/2002 | .............. A61P 39/02 |

OTHER PUBLICATIONS

Chiraz Jaafar-Maalej, Abdelhamid Elaissari, and Hatem Fessi. "Lipid-based carriers: manufacturing and applications for pulmonary route." Expert Opinion in Drug Delivery, vol. 9(9), 2012, pp. 1111-1127. (Year: 2012).*

(Continued)

*Primary Examiner* — Isaac Shomer
(74) *Attorney, Agent, or Firm* — Anova Law Group, PLLC

(57) ABSTRACT

Among others, the present invention provides a liposome comprising an active ingredient and one membrane or one inner membrane and one outer membrane. Each membrane comprises a plurality of lipid molecules, and the active ingredient is entrapped inside the interior space defined by the membrane or the inner membrane, or embodied in the membrane or membranes and form a part of the membrane (s).

9 Claims, 15 Drawing Sheets

(51) Int. Cl.

| | |
|---|---|
| ***A61K 9/1277*** | (2025.01) |
| ***A61K 47/24*** | (2006.01) |
| ***A61P 3/00*** | (2006.01) |

(56) References Cited

U.S. PATENT DOCUMENTS

| | | | | |
|---|---|---|---|---|
| 2001/0041736 | A1 | 11/2001 | Veech et al. | |
| 2009/0253781 | A1 | 10/2009 | Veech et al. | |
| 2016/0166530 | A1* | 6/2016 | Dalton | A61K 31/277 514/522 |
| 2018/0008629 | A1* | 1/2018 | Dixit | A61K 9/1271 |
| 2019/0255028 | A1 | 8/2019 | Lowery et al. | |
| 2020/0129463 | A1* | 4/2020 | Lowery | A61K 31/658 |

OTHER PUBLICATIONS

Stephen M. Berge, Lyle D. Bighley, and Donald C. Monkhouse. “Pharmaceutical Salts.” Journal of Pharmaceutical Sciences, vol. 66, No. 1, Jan. 1977, pp. 1-19. (Year: 1977).*

“2020 National Licensed Pharmacist Professional Qualification Examination Guide—Pharmacy Professional Knowledge”, Organized and compiled by the National Drug Administration Pharmacist Qualification Certification Center, China Medical Science and Technology Press, Mar. 31, 2020 (Mar. 31, 2020), pp. 250-251.

“New medicine development and research”, Editor-in-Chief: Li Quanlin, China Medical Science and Technology Press, Dec. 31, 2008 (Dec. 31, 2008), p. 656.

Industrial Pharmacy, Editor-in-Chief: Pan Weisan, China Medical Science and Technology Press, Jun. 30, 2010 (Jun. 30, 2010), p. 475.

Xiaoshan Li et al. “Progress on Dairy Cow Ketosis and Preventive Measures.” Advances in Veterinary Medicine 1 (2010): 108-111.

World Intellectual Property Organization (WIPO) International Search Report for PCT/CN2022/075372 May 5, 2022 5 pages.

Elena N. Dedkova et al., “Role of β-hydroxybutyrate, its polymer poly-β-hydroxybutyrate and inorganic polyphosphate in mammalian health and disease”, Frontiers in Physioloy., vol. 5, Jul. 17, 2014, Article 260, p. 1-22.

Terada K, “Hypophagia Induced by Endogenous or Liposome-Encapsulated 3, 4-1-40 Dihydroxybutanoic Acid.” Physiology &Behavior., vol. 38, Dec. 31, 1986, pp. 861-869.

* cited by examiner

BHB LIPOSOMES AND PREPARATION METHODS THEREOF

CROSS-REFERENCE TO RELATED APPLICATIONS

This Application is a continuation application of International Patent Application No. PCT/CN2022/075372, filed on Feb. 7, 2022, which claims priority to International Patent Application No. PCT/CN2021/074773, filed on Feb. 2, 2021, the contents of all of which are incorporated herein by reference in their entirety.

BACKGROUND OF THE INVENTION

BHB stands for β-hydroxybutyric acid (also known as β-hydroxybutyrate or 3-hydroxybutyrate), one of the three main ketone bodies (namely acetoacetate, acetone and BHB). It provides a clean burning energy source for brain and muscles. While normally human body would rely on glucose for energy, when the supply of glucose is too low for the body's energy needs, such as during periods of prolonged exercise, starvation, or absence of dietary carbohydrates, the body will turn to consume fat as fuel. Since the brain and central nervous system cannot directly use fat for energy, the liver produces ketone bodies (also known as ketones) from fatty acids as an alternative fuel source, which are then released into the blood/plasma. Ketones not only provide fuel for the brain, but are also used by the skeletal and heart muscle. Plenty of studies on exogenous ketones have shown that elevated ketone levels in blood can help improve athletic performance, recovery, appetite control and mental clarity.

Well established research data show that BHB not only can increase blood ketone levels, but also may help your body enter the state of ketosis more quickly. At the same time, BHB can help to improve endurance performance, support appetite control and provide powerful energy to the brain, bone, myocardial tissues, etc. Currently, BHB has been widely commercialized as a dietary supplement. Since the free acid form of BHB is highly hygroscopic and has low melting temperature, BHB is usually sold in the form of BHB mineral salt, such as BHB sodium, calcium, and magnesium.

Liposomes are small artificial vesicles of spherical shape that are composed of one or more lipid layers (often times bilayers). Studies have shown that liposomes can serve as useful drug carriers for encapsulating active ingredients to make them more efficient. For example, liposomal Vitamin C can reduce the degradation of vitamin C in the gastrointestinal tract, slow down its release and enhance absorption, so as to improve bioavailability. Liposomes can also alleviate the disorders that may occur in the gastrointestinal tract, which makes it possible for high-dose active ingredients to act for a long time (Maciej et al. in *J. Liposome Res*., (2019) 30(3), 227-234).

Generally, liposome has a normal vesicle structure, containing an aqueous internal cavity enclosed by a lipid bilayer membrane, in which hydrophilic or water-soluble molecules can be enclosed in the aqueous core and theoretically completely embedded, while hydrophobic or oil-soluble molecules can be embedded in the hydrophobic region of the phospholipid bilayers, forming part of the membrane. Alternatively, reverse vesicles are spherical containers in organic liquids (oils) consisting of an oily core surrounded by a reverse bilayer, which can carry oil-soluble substances, and the hydrophilic substances can be buried in the hydrophilic area in the bilayers (Tung et al. in J. Am. Chem. Soc. (2008) vol. 130 (27), 8813-8817).

Conventional methods for preparing liposomal drugs include film dispersion method, injection method, reverse phase evaporation method, double emulsion method, freeze-drying method, ultrasonic method, and high-pressure homogenization method, etc. The choice of method depends on: (1) the physical and chemical properties of the liposome and the embedded ingredients; (2) concentration of embedded ingredients; (3) the particle size of the liposome; (4) cost, reproducibility and applicability of industrialized production. For instance, Chinese patent application CN 111920702 A discloses a method for preparing liposomes by a film dispersion method; CN 110279590 A discloses a method for preparing liposomes by injection method; CN 102488656 A discloses a method for preparing liposomes by supercritical reverse phase evaporation method; and CN 102935068 A discloses a freeze-drying method for preparing liposomes.

Nevertheless, there remain various technical problems for those prior liposomal formulations and preparation methods, such as low effective components of liposome and difficulty for large scale production.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

This invention generally relates to formulations of β-hydroxybutyric acid (BHB) liposomes, and methods for producing such BHB liposomes. Particularly, the BHB liposomes of the present invention comprise lipids (e.g., phospholipids) and active ingredients (e.g., BHB free acid, physiologically acceptable salt, ester, or a mixture thereof, and optionally one or more additional hydrophilic ingredients), and capable of effectively delivering BHB. Such BHB liposomes can be produced by improved preparation methods of the present invention, and used for increasing or sustaining blood ketone level in a subject.

One aspect of this invention provides a liposome comprising an active ingredient and one membrane, or one inner membrane and one outer membrane, wherein the one membrane or each of the inner and outer membranes defines an interior space within the one membrane or the inner membrane, and/or between the inner and outer membranes, each membrane comprises a plurality of lipid molecules, and the active ingredient is entrapped inside the interior space or embodied in the membrane or membranes. The lipids comprise phospholipids, and the active ingredient comprises β-hydroxybutyrate acid (BHB), a physiologically acceptable salt, ester, or mixture thereof.

In some embodiments, the active ingredient is the free acid form of BHB.

In some embodiments, the BHB is in R-form, S-form or a mixture of R- and S-form. Preferably, the BHB is in R-form.

In some embodiments, depending on the proportion of components, the BHB liposome has a normal vesicle structure, wherein the BHB is entrapped inside the interior space defined by the membrane or the inner membrane.

In some embodiments, each membrane is a bilayer membrane.

In some embodiments, the liposome comprises one membrane.

In some other embodiments, depending on the proportion of components, the BHB liposome has a reverse vesicle structure, wherein the BHB is embodied in the membrane and forms a part of the membrane.

In some embodiments, the active ingredient comprises a BHB and/or one or more additional hydrophilic components, with a mass percentage ranging from 1% to 95% of the liposome's total mass. Examples of hydrophilic components include, but not limited to, vitamin C, vitamin B1, vitamin B6, folic acid and other water-soluble vitamins.

In some further embodiments, the active ingredient has a mass percentage ranging from 60% to 85% of the total mass of the liposome.

In some embodiments, the phospholipid comprises phosphatidylcholine, phosphatidylethanolamine, phosphatidylserine, phosphatidylinositol, lysophosphatidylcholine, lysophosphatidylethanolamine, dipalmitoyl phosphatidylcholine, dioleoyl phosphatidylcholine, dilinoleoyl phosphatidylcholine, distearoyl phosphatidylcholine, phosphatidylcholine, or a combination thereof (e.g., a mixture of any two or any three in any ratio).

In some embodiments, the phospholipid is phosphatidylcholine.

In some embodiments, the lipid has a mass percentage ranging from 1% to 40% of the total mass of the liposome. Preferably, the lipids have a mass percentage ranging from 5% to 10% of the liposome's total mass.

In some embodiments, the BHB liposome further comprises co-emulsifier(s). Examples of suitable co-emulsifier include polyethylene glycol 200-2000, glycerol, sorbitol or a combination thereof (e.g., a mixture of any two or any three in any ratio).

In some embodiments, the co-emulsifier has a mass percentage ranging from 1% to 40% (e.g., from 5% to 10%) of the total mass of the liposome.

In some embodiments, the BHB liposome further comprises stabilizer(s). Examples of stabilizers include, but not limited to, medium-chain fatty acid glycerides, soybean oil, sunflower oil, or a combination thereof (e.g., a mixture of any two or any three in any ratio).

In some embodiments, the stabilizer has a mass percentage ranging from 1% to 40%, or preferably from 5% to 10% of the liposome's total mass.

In some embodiments, the BHB liposome further includes a solvent (e.g., water). The mass percentage of the solvent ranges from 0.01% to 10%, or preferably from 0.01% to 1%, of the liposome's total mass.

In some embodiments, the BHB liposome of the present invention comprises: (a) an active ingredient which includes BHB or its salt or ester; (b) a phospholipid; (c) a co-emulsifier; (d) a stabilizer; and (e) water.

In some embodiments, the BHB liposome comprises (a) the active ingredient, with a mass percentage ranging from 1% to 95%; (b) the phospholipid, with a mass percentage ranging from 1% to 40%; (c) the co-emulsifier, with a mass percentage ranging from 1% to 40%; (d) the stabilizer, with a mass percentage ranging from 1% to 40%; and (e) water, with a mass percentage ranging from 0.01% to 10% of the liposome's total mass.

In some further embodiments, the BHB liposome comprises (a) the active ingredient, with a mass percentage ranging from 60% to 85%; (b) the phospholipid, with a mass percentage ranging from 5% to 10%; (c) the co-emulsifier, with a mass percentage ranging from 5% to 10%; (d) the stabilizer with a mass percentage ranging from 5% to 10%; and (e) water, with a mass percentage ranging from 0.01% to 1% of the liposome's total mass.

In some embodiments, the active ingredient comprises a BHB and optionally one or more additional hydrophilic components. Examples of hydrophilic components include, but not limited to, water-soluble vitamins, for example, vitamin C, vitamin B1, vitamin B6, folic acid, or any mixture thereof.

In some embodiments, the phospholipid comprises phosphatidylcholine, phosphatidylethanolamine, phosphatidylserine, phosphatidylinositol, lysophosphatidylcholine, lysophosphatidylethanolamine, dipalmitoyl phosphatidylcholine, dioleoyl phosphatidylcholine, dilinoleoyl phosphatidylcholine, distearoyl phosphatidylcholine, phosphatidylcholine, or a combination thereof.

In some embodiments, the co-emulsifier comprises polyethylene glycol 200-2000, glycerol, sorbitol or a combination thereof.

In some embodiments, the stabilizer comprises medium-chain fatty acid glycerides, soybean oil, sunflower oil, or a combination thereof.

Another aspect of this invention provides methods for preparing the BHP liposome. In particular, the method comprises preparation of a BHB coarse suspension.

In some embodiments, the method for preparing a BHP liposome comprises the steps of: melting crystalline BHB; dissolving phospholipid; preparing a BHB coarse suspension; and preparation of the BHB liposome.

In some embodiments, melting crystalline BHB comprises heating crystalline BHB at a desired temperature (e.g., 50-80° C.) for a period (e.g., 10-60 minutes) until melting to a clear liquid state.

In some embodiments, the phospholipid dissolution comprises mixing phospholipids and stabilizers, heating them at a desired temperature (e.g., 50-80° C.) for a period (e.g., 10-60 minutes), to obtain a yellow liquid.

In some embodiments, the preparation of BHB coarse suspension comprises mixing water, co-emulsifiers and the molten BHB liquid, adding the solution of phospholipids and stabilizers from the previous step to the mixture, and mixing them for a period (e.g., 5-30 minutes) to obtain the BHB coarse suspension by using a mixing equipment.

In some embodiments, the preparation of BHB liposomes comprises homogenizing the BHB coarse suspension to obtain BHB liposomes by using a liposomal preparation equipment.

In some other embodiments, the method for preparing the BHP liposome comprises the steps of: melting crystalline BHB; preparation of a BHB coarse suspension; and preparation of BHB liposome.

In some embodiments, melting crystalline BHB comprises heating crystalline BHB at a desired temperature (e.g., 50-80° C.) for a period (e.g., 10-60 minutes) till melting to a clear liquid state.

In some embodiments, the preparation of BHB coarse suspension comprises dissolving the molten BHB liquid and phospholipids in an organic solvent, and then removing the organic solvent through evaporation in order to form a uniformly-spread lipid film, and then adding water, co-emulsifier, and stabilizer to the lipid film, and dispersing for a period of time (e.g., 5-30 minutes) to obtain the BHB coarse suspension by using a mixing equipment.

In some embodiments, the preparation of BHB liposome comprises homogenizing the BHB coarse suspension to obtain BHB liposomes by using a liposomal preparation equipment.

Examples of mixing equipment include, but not limited to, a high-shear emulsifier and/or a high-speed disperser.

Examples of liposomal preparation equipment include, but not limited to, nano-liposome extruder, high-pressure homogenizer, high-pressure microfluidic system and/or ultrasonic cell disruption.

In yet another aspect, the present invention provides a method for increasing or sustaining blood ketone level in a subject, comprising administration the inventive BHB liposome according to the invention.

In some embodiments, the subject is a human.

As used herein, the term "or" is meant to include both "and" and "or." In other words, the term "or" may also be replaced with "and/or."

As used herein, the singular forms "a," "an" and "the" are intended to include the plural forms as well, unless the context clearly indicates otherwise.

BRIEF DESCRIPTIONS OF THE FIGURES

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION OF THE INVENTION

Reference will now be made in detail to the preferred embodiments of the invention, examples of which are further illustrated. While the invention will be described in conjunction with the preferred embodiments, it will be understood that they are not intended to limit the invention to these embodiments. To the contrary, the invention is intended to cover alternatives, modifications and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and other features have not been described in detail as not to unnecessarily obscure aspects of the present invention.

Definitions

As used herein, the term "subject" or "patient" is used interchangeably and as used herein mean any mammal including but not limited to human beings including a human patient or subject to which the compositions of the invention can be administered. The term "mammal" includes human patients and non-human primates, as well as experimental animals such as rabbits, rats, and mice, and other animals.

Chemical structure of β-hydroxybutyrate, also known as 3-hydroxybutyrate, β-HB, BHB, or beta-hydroxybutyrate, is shown below.

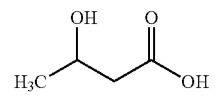

BHB is a chiral molecule at the 3' hydroxyl group, and there are two enantiomers, R/D and S/L.

The term "Amphiphile" refers to a molecule consisting of a water-soluble (hydrophilic) and an organic solvent-soluble (lipophilic) moiety. Amphipathic lipids are usually the major component of a lipid vesicle.

General

Generally speaking, various embodiments of the present invention provide formulations of BHB liposome, comprising lipids (e.g., phospholipids), an active ingredient (e.g., β-hydroxybutyric acid (BHB), physiologically acceptable salt, ester, or a mixture thereof, and optionally one or more additional hydrophilic active ingredients), a co-emulsifier, a stabilizer, and a solvent (e.g., water). In some embodiments, the BHB liposomes according to the present invention are made from the following raw materials by mass: (a) active ingredients: 1~95%; (b) phospholipids: 1~40%; (c) co-emulsifiers: 1~40%; (d) stabilizers: 1~40%; and (e) water: 0.01~10%.

In some preferred embodiments, the BHB liposomes according to the present invention are preferably made from the following raw materials by mass: (a) active ingredients: 60-85%; (b) phospholipids: 5~10%; (c) co-emulsifiers: 5~10%; (d) stabilizers: 5~10%; and (e) water: 0.01~1%.

Figure 1:
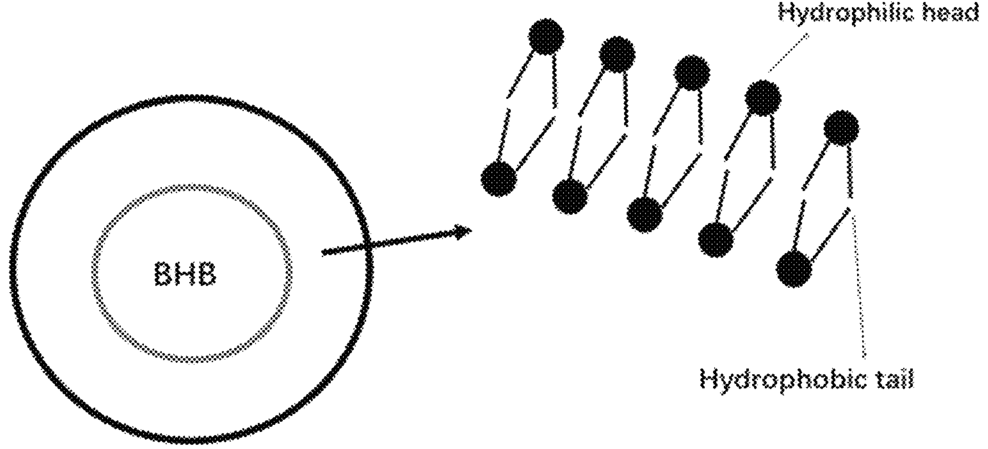
FIG. 1 shows a β-hydroxybutyric acid (BHB) liposome according to one embodiment of this invention, in the form of normal vesicles.
Figure 2:
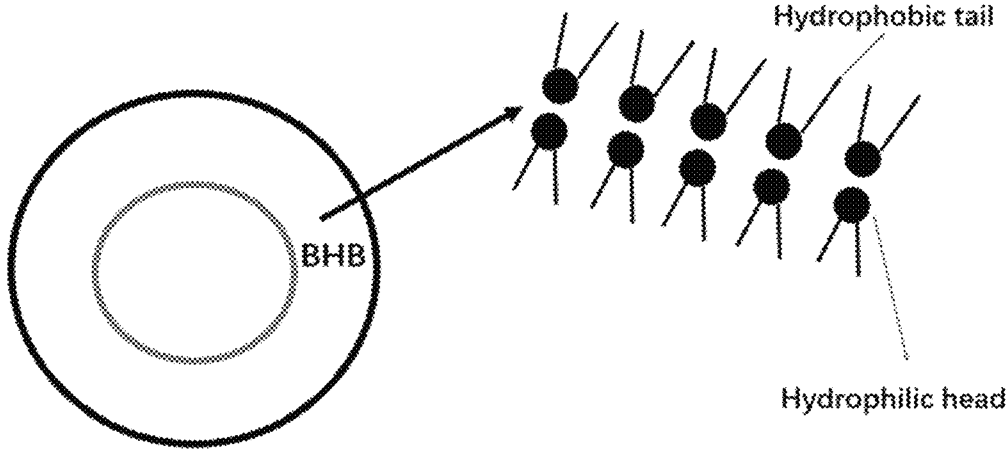
FIG. 2 shows a BHB liposome according to another embodiment of this invention, in the form of reverse vesicles.

The BHB liposomes according to the present invention can be in the form of either normal vesicle structures or reverse vesicle structures, depending on the proportion of components. As shown in FIG. 1, for normal vesicles, the membranes are composed of one or more phospholipid bilayers, with the hydrophilic head groups arranged around the periphery. Accordingly, the hydrophilic BHB is located inside the aqueous core surrounded by the lipid bilayer membrane. Alternatively, as shown in FIG. 2, the BHB liposomes may form reverse vesicles, composed of a bilayer with the hydrophilic head groups arranged internally, surrounding a nonpolar core. Accordingly, the hydrophilic BHB is embedded in the lipid bilayer membrane, and form a part of the membrane.

The present invention also provides methods for producing such BHB liposomes, including, among other things, preparation of a BHB coarse suspension.

More specifically, one exemplary preparation method according to the present invention includes: (1) melting crystalline BHB: heating crystalline BHB free acid at 50-80° C. for 10-60 minutes till melting to a clear liquid state; (2) Phospholipid dissolution: mixing phospholipids and stabilizers, heating them at 50-80° C. for 10-60 minutes to obtain a yellow liquid; (3) preparation of the BHB coarse suspension: mixing water, co-emulsifiers and the molten BHB liquid from step 1, adding the solution of phospholipids and stabilizers from step 2 to the mixture, and stirring continuously for 5-30 minutes to obtain the BHB coarse suspension by using a mixing equipment; and (4) preparation of BHB liposomes: homogenizing the BHB coarse suspension to obtain BHB liposomes by using a conventional liposomal preparation equipment.

Another exemplary preparation method according to the present invention includes: (1) melting crystalline BHB: heating crystalline BHB at 50-80° C. for 10-60 minutes till melting to a clear liquid state; (2) preparation of the BHB coarse suspension: dissolving the molten BHB liquid from step 1 and phospholipids in an organic solvent, and then removing the organic solvent through evaporation to form a uniformly-spread lipid film, then adding water, co-emulsifiers, and stabilizers to the lipid film, and dispersing for 5-30 minutes to obtain the BHB coarse suspension by using a mixing equipment; (3) preparation of BHB liposomes: homogenizing the BHB coarse suspension to obtain BHB liposomes by using a conventional liposomal preparation equipment.

The following examples are illustrative of select embodiments of the present invention and are not meant to limit the scope of the invention.

Example 1

The BHB liposome formulation in Example 1 is made of the raw materials with the respective mass percentages as show in Table 1 below.

TABLE 1

| Formulation ingredient | Mass (kg) | Mass percentage (%) |
|---|---|---|
| BHB free acid | 1.00 | 10.00 |
| Phosphatidylcholine | 2.00 | 20.00 |
| Glycerol | 2.00 | 20.00 |
| Medium-chain fatty acid glycerides | 4.00 | 40.00 |
| Water | 1.00 | 10.00 |

The above-mentioned BHB liposome formulation is prepared as follows:

(1) Melting crystalline BHB: Heat 1 kg crystalline BHB in a 50° C. water bath for 60 minutes till melting to a clear liquid state;

(2) Phospholipid dissolution: Mix 2 kg of phosphatidylcholine and 4 kg of medium-chain fatty acid glycerides, heat them in a 50° C. water bath for 60 minutes to obtain a yellow liquid;

(3) Preparation of BHB coarse suspension: Mix 1 kg of water, 2 kg of glycerol, and 1 kg of BHB melting liquid, add the yellow liquid of 2 kg of phosphatidylcholine and 4 kg of medium-chain fatty acid glycerides from step 2 to the mixture, and then stir the mixture for minutes to obtain the BHB coarse suspension by using the high-shear emulsifier;

(4) Preparation of BHB liposomes: Pass the BHB coarse suspension through a filter with defined pore size under high pressure (6000 psi) by using the liposome extruder system to obtain the uniform BHB liposome, in which the solid content of BHB is 10%.

Example 2

The BHB liposome formulation in Example 2 is made of the raw materials with the respective mass percentages in Table 2 below.

TABLE 2

| Formulation Ingredient | Mass (kg) | Mass percentage (%) |
|---|---|---|
| BHB free acid | 1.00 | 10.00 |
| Phosphatidylcholine | 2.00 | 20.00 |
| Glycerol | 2.00 | 20.00 |
| Medium-chain fatty acid glycerides | 4.00 | 40.00 |
| Water | 1.00 | 10.00 |

The above-mentioned BHB liposome formulation is prepared as follows:

(1) Melting crystalline BHB: Heat 1 kg crystalline BHB in a 50° C. water bath for 60 minutes till melting to a clear liquid state;

(2) Preparation of BHB coarse suspension: Mix 1 kg BHB melting liquid and 2 kg of phosphatidylcholine, dissolve them in 10 kg ethanol, and then remove the ethanol through evaporation to form a uniformly-spread lipid film, then add 1 kg water, 2 kg glycerol, 4 kg medium-chain fatty acid glyceride to the lipid film, disperse for 30 minutes to obtain the BHB coarse suspension by using a high-shear emulsifier;

(3) Preparation of BHB liposomes: Pass the BHB coarse suspension through a filter with defined pore size under high pressure (6000 psi) by using a liposome extruder system to obtain the uniform BHB liposome, in which the solid content of BHB is 10%.

Example 3

The BHB liposome formulation in Example 3 is made of the raw materials with the respective mass percentages as shown in Table 3 below.

TABLE 3

| Formulation ingredient | Mass (kg) | Mass percentage (%) |
|---|---|---|
| BHB free acid | 3.00 | 30.00 |
| Phosphatidylethanolamine | 1.00 | 10.00 |
| Polyethylene glycol 400 | 1.00 | 10.00 |
| Soybean oil | 4.00 | 40.00 |
| Water | 1.00 | 10.00 |

The above-mentioned formulation of BHB liposome is prepared as follows:

(1) Melting crystalline BHB: Heat 3 kg crystalline BHB in a 50° C. water bath for 60 minutes till melting to a clear liquid state;

(2) Phospholipid dissolution: Mix 1 kg of phosphatidylethanolamine and 4 kg of soybean oil, heat them in a 50° C. water bath for 60 minutes to obtain a yellow liquid;

(3) Preparation of BHB coarse suspension: Mix 1 kg of water, 1 kg of polyethylene glycol 400, and 3 kg of BHB melting liquid, and add the yellow liquid of 1 kg of phosphatidylethanolamine and 4 kg of soybean oil from step 2 to the mixture, and disperse the mixture for 30 minutes to obtain the BHB coarse suspension by using a high-speed disperser;

(4) Preparation of BHB liposomal: Pressurize the BHB coarse suspension (6000 psi) by using the high-pressure microfluidic system to obtain homogenized BHB liposome, in which the solid content of BHB is 30%.

Example 4

The BHB liposome formulation in Example 4 is made of the raw materials with the respective mass percentages as shown in Table 4 below.

TABLE 4

| Formulation Ingredient | Mass (kg) | Mass percentage (%) |
|---|---|---|
| BHB free acid | 5.00 | 50.00 |
| Phosphatidylserine | 1.00 | 10.00 |
| Sorbitol | 1.00 | 10.00 |
| Sunflower oil | 2.90 | 29.00 |
| Water | 0.10 | 1.00 |

The above-mentioned BHB liposome formulation is prepared as follows:

(1) Melting crystalline BHB: Heat 5 kg of crystalline BHB in a 50° C. water bath for 60 minutes till melting to a clear liquid state;

(2) Phospholipid dissolution: Mix 1 kg phosphatidylserine and 2.9 kg sunflower oil, heat them in a 50° C. water bath for 60 minutes to obtain a yellow liquid;

(3) Preparation of BHB coarse suspension: Mix 0.1 kg water, 1 kg sorbitol, and 5 kg BHB melting liquid, and add the yellow liquid of 1 kg phosphatidylserine and 2.9 kg sunflower oil from step 2 to the mixture, and stir the mixture for 30 minutes to obtain the BHB coarse suspension by using the high-shear emulsifier;

(4) Preparation of BHB liposome: Homogenize the BHB coarse suspension twice using a high-pressure homogenizer at the pressure of 35-45 MPa for the first time and 60-70 MPa for the second time to obtain the uniform BHB liposome, in which the solid content of BHB is 50%.

Example 5

The BHB liposome formulation in Example 5 is made of the raw materials with the respective mass percentages as shown in Table 5 below.

TABLE 5

| Formulation Ingredient | Mass (kg) | Mass percentage (%) |
|---|---|---|
| BHB free acid | 5.00 | 50.00 |
| Phosphatidylserine | 1.00 | 10.00 |
| Sorbitol | 1.00 | 10.00 |
| Sunflower oil | 2.90 | 29.00 |
| Water | 0.10 | 1.00 |

The above-mentioned BHB liposome formulation is prepared as follows:

(1) Melting crystalline BHB: Heat 5 kg crystalline BHB in a 50° C. water bath for 60 minutes till melting to a clear liquid state.

(2) Preparation of BHB coarse suspension: Mix 5 kg BHB melting liquid and 1 kg phosphatidylcholine, dissolve them in 10 kg ethanol, and then remove the ethanol by evaporation to form a uniformly-spread lipid film, then add 0.1 kg water, 1 kg sorbitol and 2.9 kg sunflower oil to the lipid film, and disperse for 30 minutes to obtain the BHB coarse suspension by using the high-shear emulsifier;

(3) Preparation of BHB liposomal: Homogenize the BHB coarse suspension twice using a high-pressure homogenizer at the pressure of 35-45 MPa for the first time and 60-70 MPa for the second time to obtain the uniform BHB liposome, in which the solid content of BHB is 50%.

Example 6

The BHB liposome formulation in Example 6 is made of the raw materials with the respective mass percentages as shown in Table 6 below.

TABLE 6

| Formulation ingredient | Mass (kg) | Mass percentage (%) |
|---|---|---|
| BHB free acid | 7.00 | 70.00 |
| Phosphatidylcholine | 0.60 | 6.00 |
| Polyethylene glycol 400 | 0.60 | 6.00 |
| Medium-chain fatty acid glycerides | 1.74 | 17.40 |
| Water | 0.06 | 0.60 |

The above-mentioned BHB liposome formulation is prepared as follows:

(1) Melting crystalline BHB: Heat 7 kg crystalline BHB in an 80° C. water bath for 20 minutes till melting to a clear liquid state;

(2) Phospholipid dissolution: Mix 0.6 kg of phosphatidylcholine and 1.74 kg of medium-chain fatty acid glycerides, heat them in the 80° C. water bath for 20 minutes to obtain a yellow liquid;

(3) Preparation of BHB coarse suspension: Mix 0.06 kg of water, 0.6 kg of polyethylene glycol 400, 7 kg of BHB melting liquid, and add the yellow liquid of 0.6 kg of phosphatidylcholine and 1.74 kg of medium-chain fatty acid glycerides from step 2 to the mixture, and stir for 30 minutes to obtain the BHB coarse suspension by using a high-shear emulsifier;

(4) Preparation of BHB liposome: Pass the BHB coarse suspension through a filter with defined pore size under high pressure (6000 psi) by using a liposome extruder system to obtain the uniform BHB liposome, in which the solid content of BHB is 70%.

Example 7

The BHB liposome formulation in Example 7 is made of the raw materials with the respective mass percentages as shown in Table 7 below.

TABLE 7

| Formulation Ingredient | Mass (kg) | Mass percentage (%) |
|---|---|---|
| BHB free acid | 8.00 | 80.00 |
| Phosphatidylinositol | 0.60 | 6.00 |
| Polyethylene glycol 400 | 0.60 | 6.00 |
| Soybean oil | 0.74 | 7.40 |
| Water | 0.06 | 0.60 |

The above-mentioned BHB liposome formulation is prepared as follows:

(1) Melting crystalline BHB: Heat 8 kg of BHB free acid crystals in an 80° C. water bath for 20 minutes till melting to a clear liquid state;

(2) Preparation of BHB coarse suspension: Mix 8 kg of BHB melting liquid and 0.6 kg of phosphatidylcholine, dissolve them in 10 kg ethanol, and then remove the ethanol by evaporation to form a uniformly-spread lipid film, then add 0.06 kg of water, 0.6 kg of polyethylene glycol 400, 0.74 kg of soybean oil to the lipid film, and stir for 30 minutes to obtain the BHB coarse suspension by using the high-shear emulsifier;

(3) Preparation of BHB liposomal: Pass the BHB coarse suspension through a filter with defined pore size under high pressure (6000 psi) by using the liposome extruder system to obtain the uniform BHB liposome, in which the solid content of BHB is 80%.

Example 8

The BHB liposome formulation in Example 8 is made of the raw materials with the respective mass percentages as shown in Table 8 below.

TABLE 8

| Formulation Ingredient | Mass (kg) | Mass percentage (%) |
|---|---|---|
| BHB free acid | 8.00 | 80.00 |
| Phosphatidylinositol | 0.60 | 6.00 |
| Polyethylene glycol 400 | 0.60 | 6.00 |
| Soybean oil | 0.74 | 7.40 |
| Water | 0.06 | 0.60 |

The above-mentioned BHB liposome formulation is prepared as follows:

(1) Melting crystalline BHB: Heat 8 kg of BHB free acid crystals in an 80° C. water bath for 20 minutes till melting to a clear liquid state;

(2) Phospholipid dissolution: Mix 0.6 kg of phosphatidylinositol with 0.74 kg of soybean oil, heat them in the 80° C. water bath for 20 minutes to obtain a yellow liquid;

(3) Preparation of BHB coarse suspension: Mix 0.06 kg of water, 0.6 kg of polyethylene glycol 400, 8 kg of BHB melting liquid, then add the yellow liquid of 0.6 kg of phosphatidylinositol and 0.74 kg of soybean oil from step 2 to the mixture, and stir for 30 minutes to obtain the BHB coarse suspension by using the high-shear emulsifier;

(4) Preparation of BHB liposomal: Pass the BHB coarse suspension through a filter with defined pore size under high pressure (6000 psi) by using a liposome extruder system to obtain the uniform BHB liposome, in which the solid content of BHB is 80%.

Example 9 Stability Analysis of the BHB Liposomes

We performed this study to evaluate the stability of BHB liposomes after long-term storage under conventional condition (20° C. and 60% relative humidity) and under cold condition (5° C.). This study was conducted by measuring the sample of BHB liposome using HPLC method initially and at week 1, week 2, week 3, week 4. FIGS. 3 and 4 show the results of the stability analysis. As shown in the Figures, peaks labeled with BHB indicate BHB dry content, and peaks labeled with BHB dimers or BHB trimers indicate degradation products and impurities of BHB.

Figure 3A:
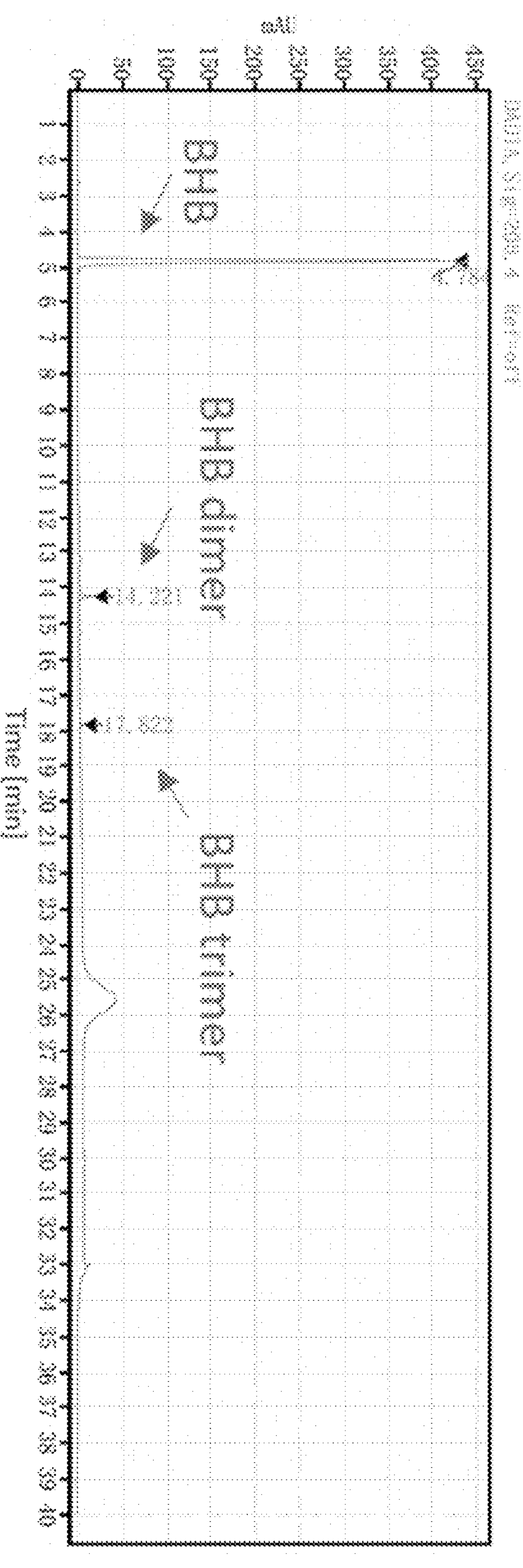
FIGS. 3A-3G show the stability of BHB liposomes after long term storage under cold condition (5° C.). Peaks labeled with BHB indicate BHB dry content, and peaks labeled with BHB dimers or BHB trimers indicate degradation products and impurities of BHB.
Figure 3B:
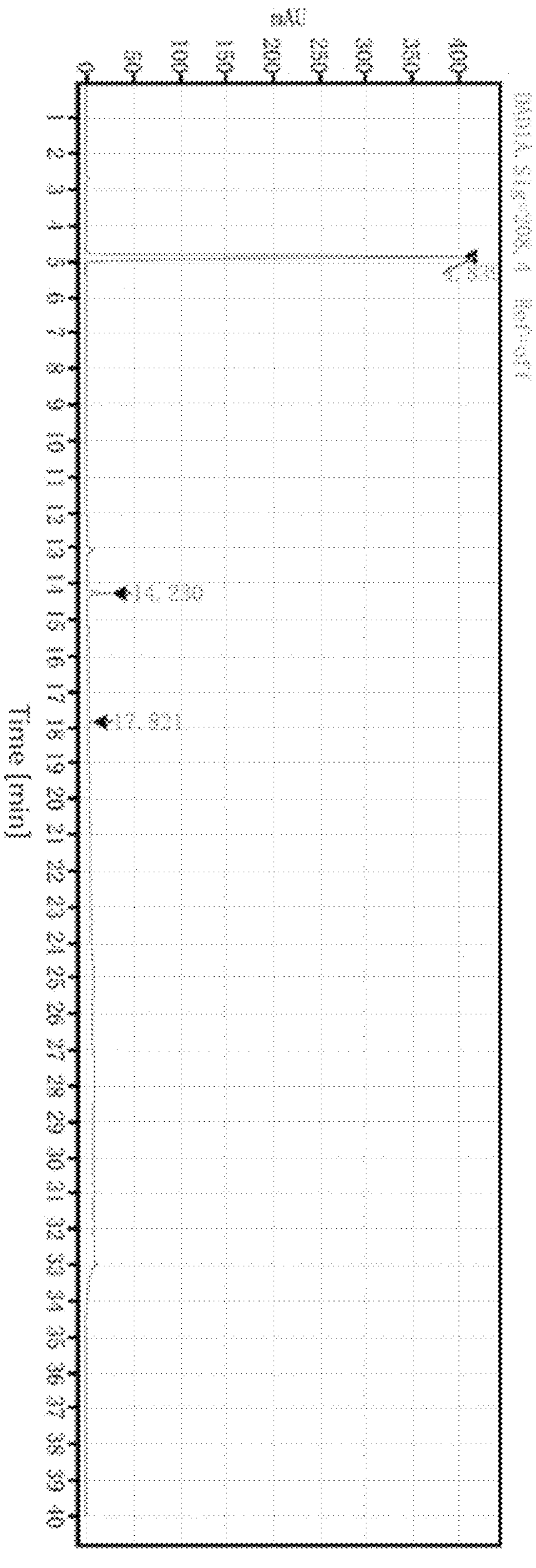
Figure 3C:
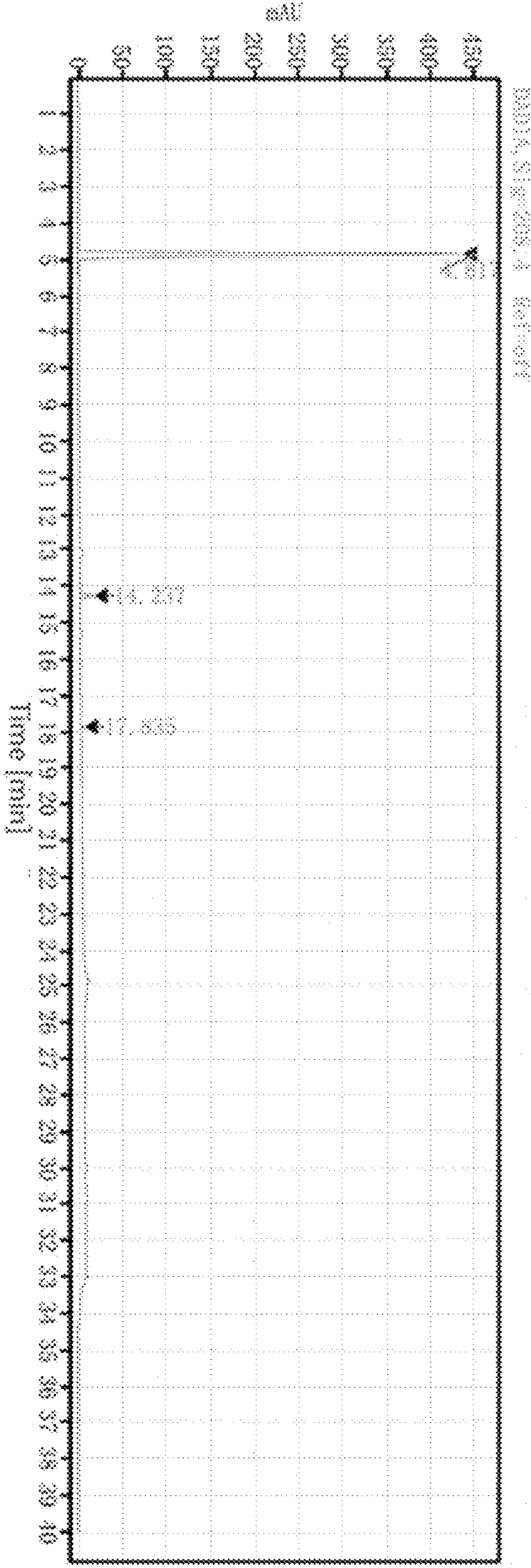
Figure 3D:
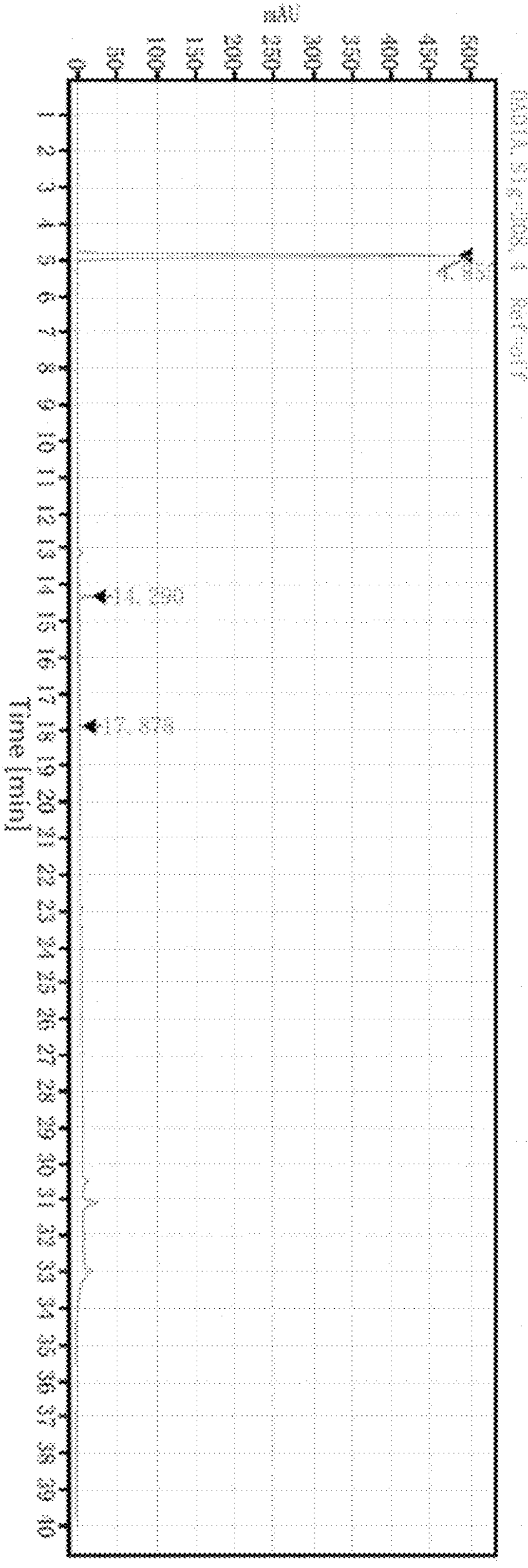
Figure 3E:
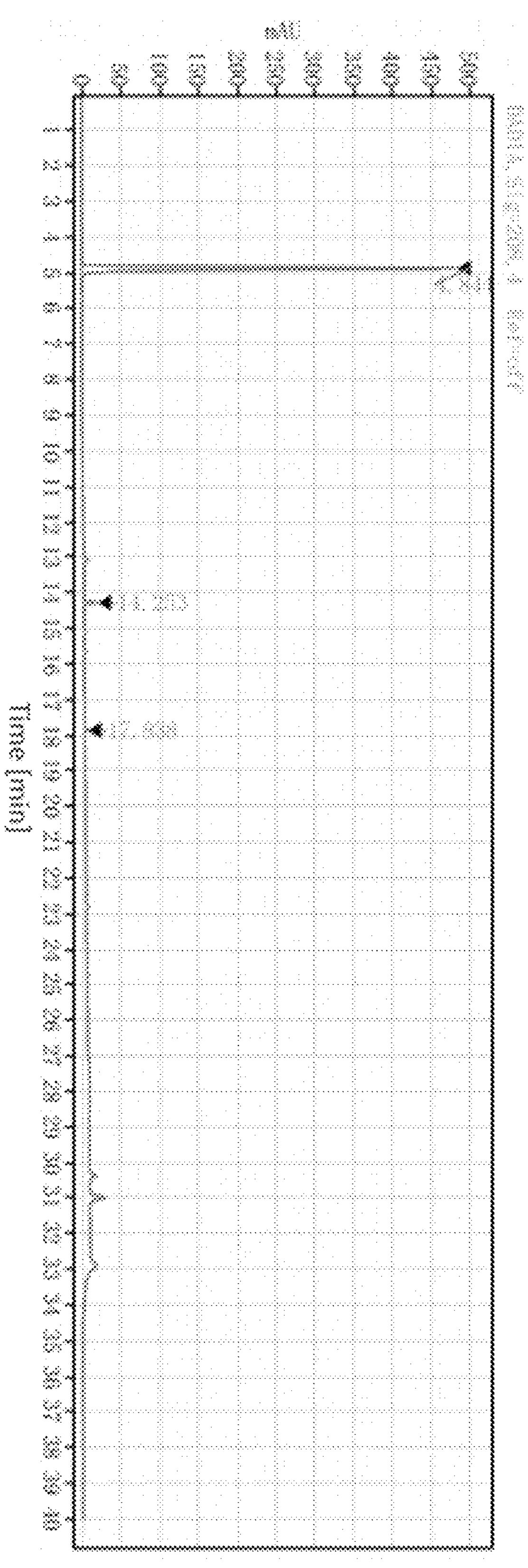
Figure 3F:
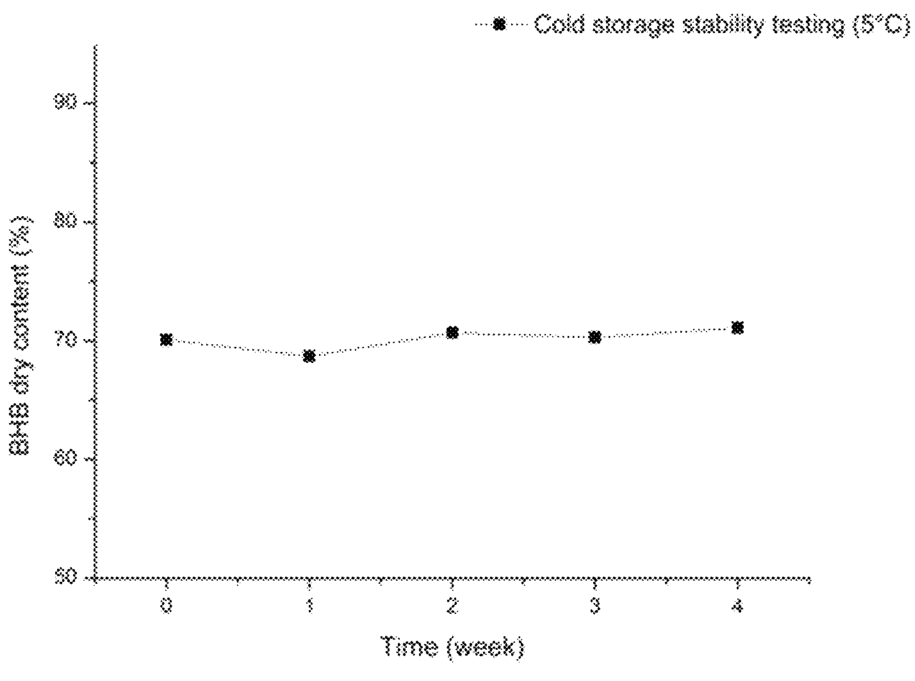
Figure 3G:
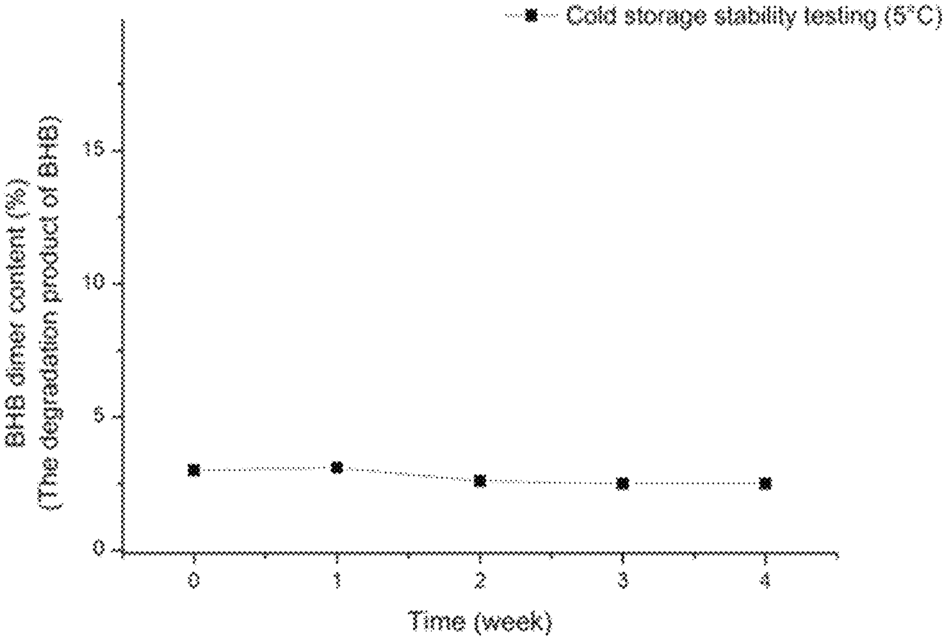

FIGS. 3A-3G show the stability of BHB liposome after long-term storage under cold condition (5° C.). More specifically, FIG. 3A shows HPLC analysis results of the initial BHB liposome (week 0). FIG. 3B shows HPLC analysis results of BHB liposome after 1-week storage under cold condition (5° C.). FIG. 3C shows HPLC analysis results of BHB liposome after 2-week storage under cold condition (5° C.). FIG. 3D shows HPLC analysis results of BHB liposome after 3-week storage under cold condition (5° C.). FIG. 3E shows HPLC analysis results of BHB liposome after 4-week storage under cold condition (5° C.). FIG. 3F shows BHB dry content (%) of BHB liposome stored under cold condition. FIG. 3G shows BHB dimer content (%) of BHB liposome stored under cold condition (BHB dimer indicates the degradation product of BHB).

Figure 4A:
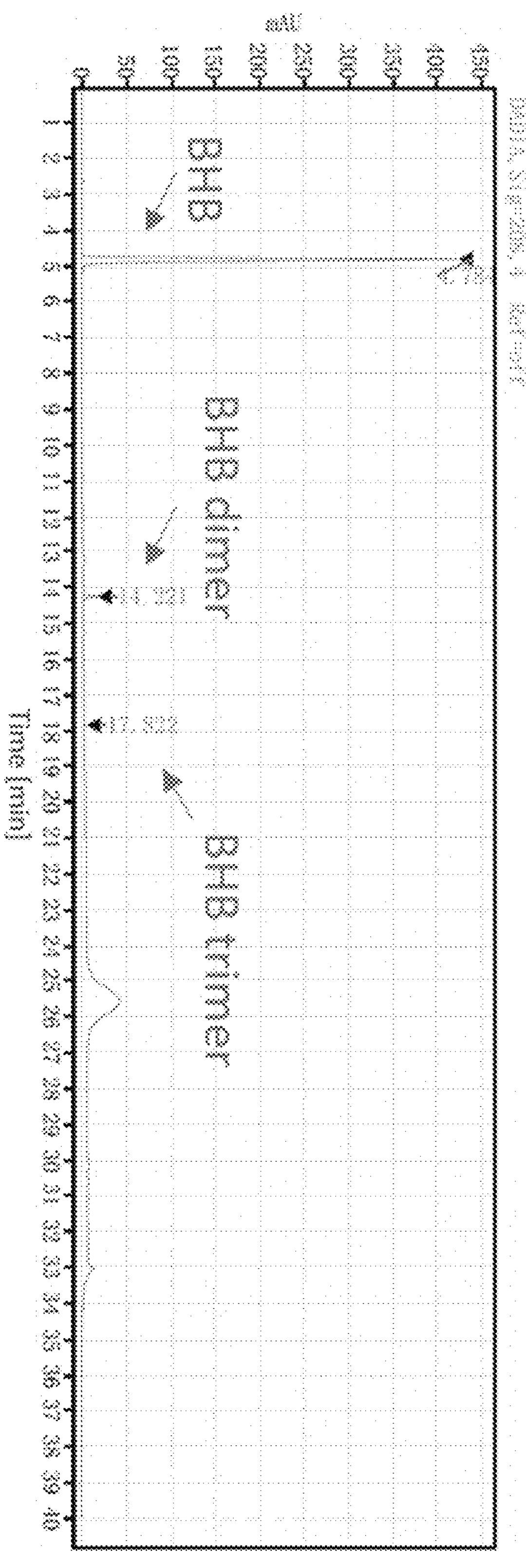
FIGS. 4A-4G show the stability of BHB liposomes after long term storage under conventional condition (20° C. and 60% relative humidity). Peaks labeled with BHB indicate BHB dry content, and peaks labeled with BHB dimers or BHB trimers indicate degradation products and impurities of BHB.
Figure 4B:
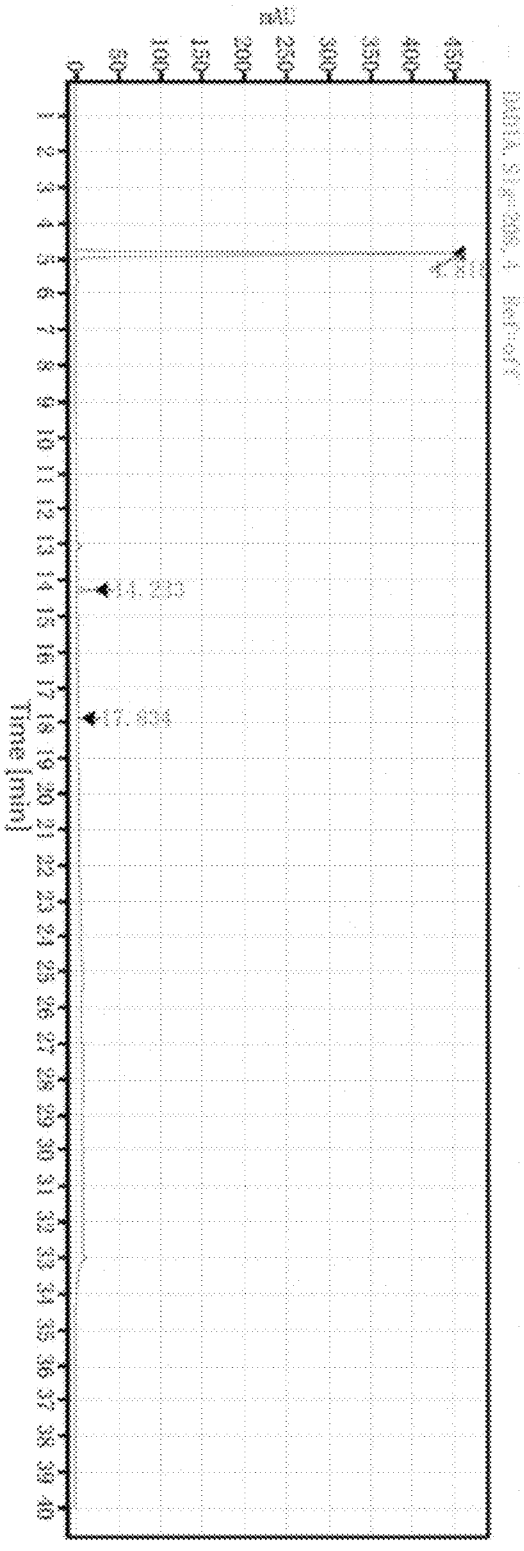
Figure 4C:
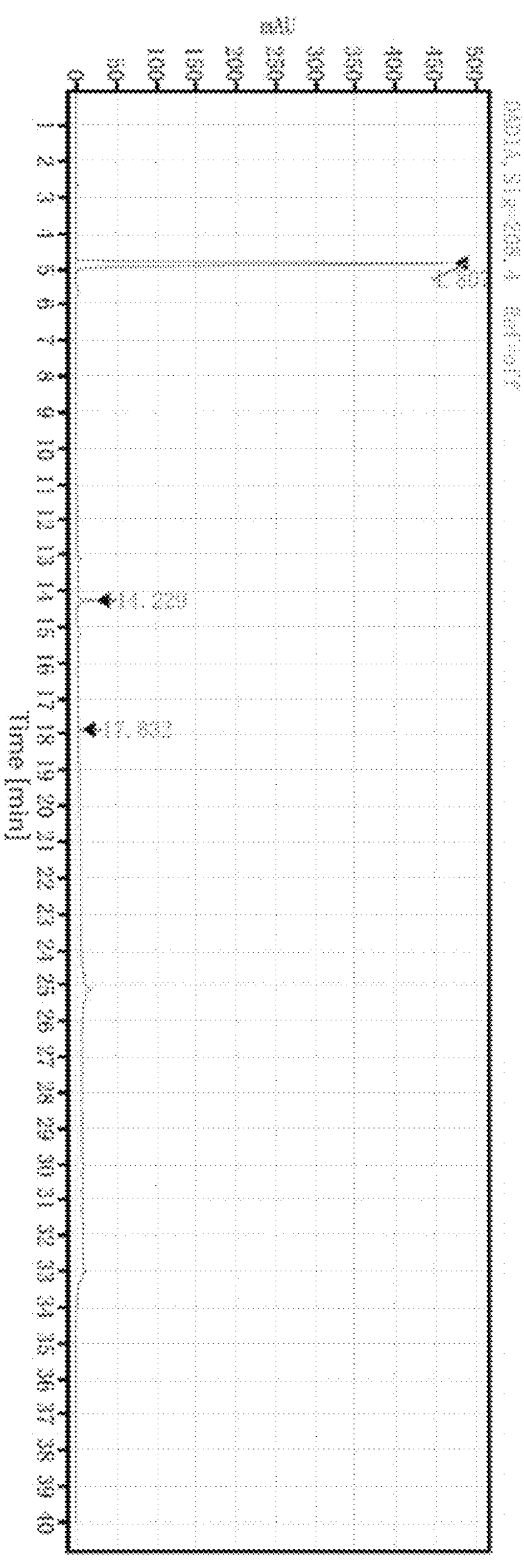
Figure 4D:
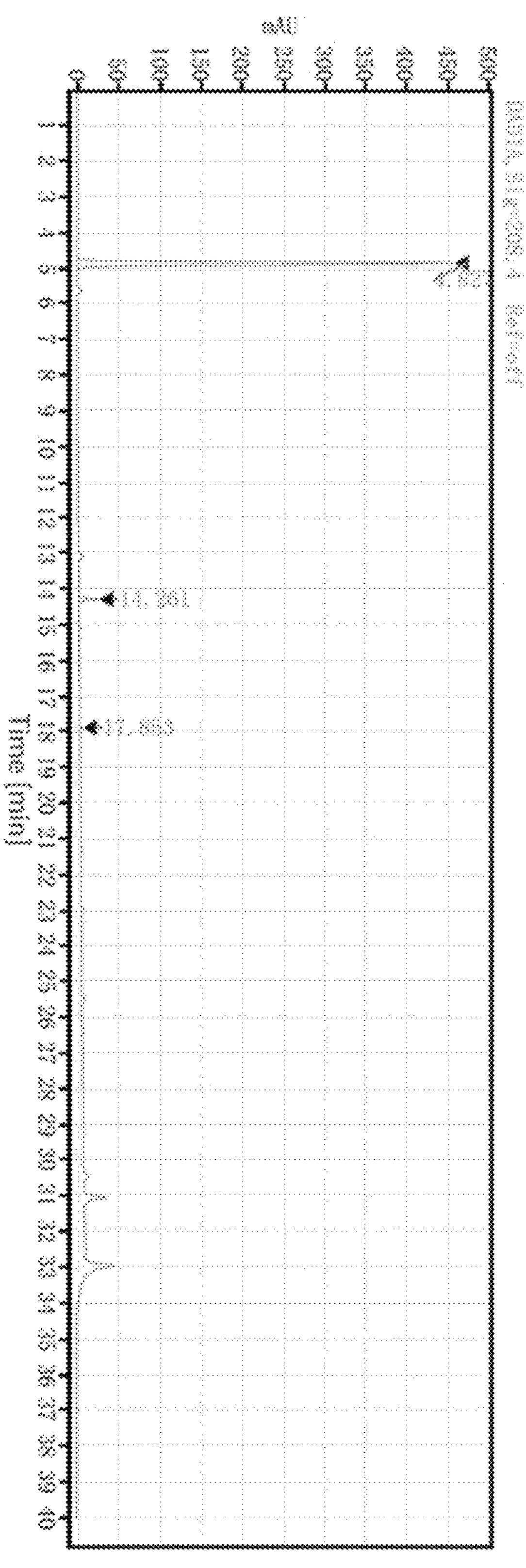
Figure 4E:
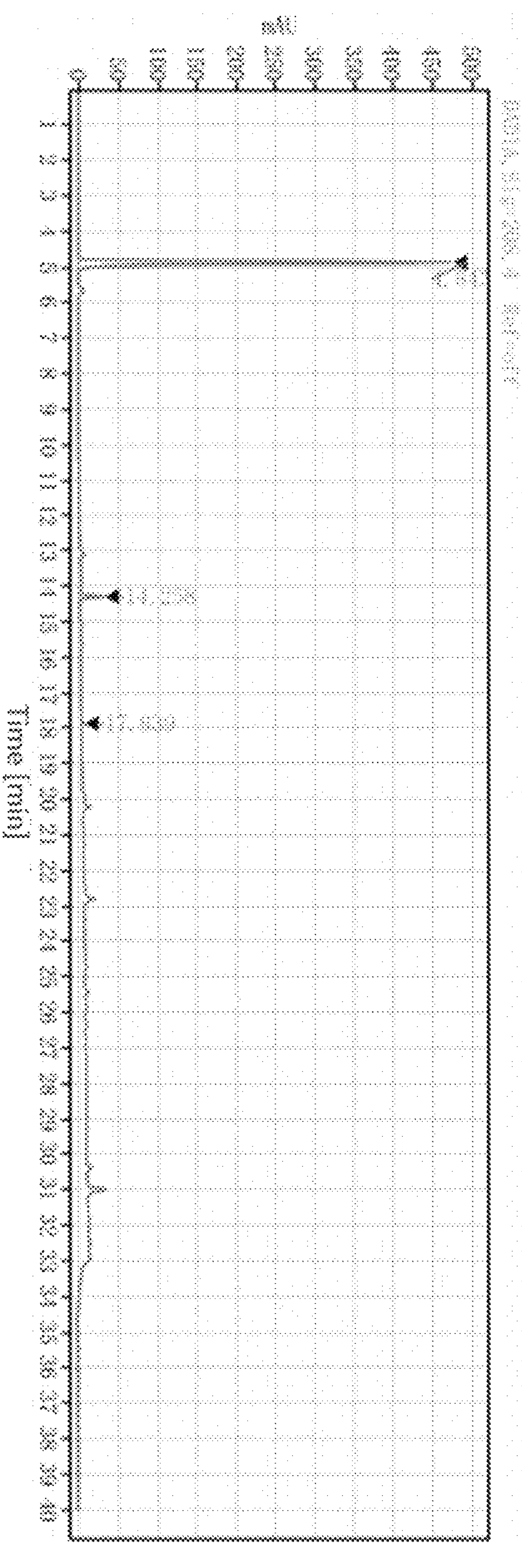
Figure 4F:
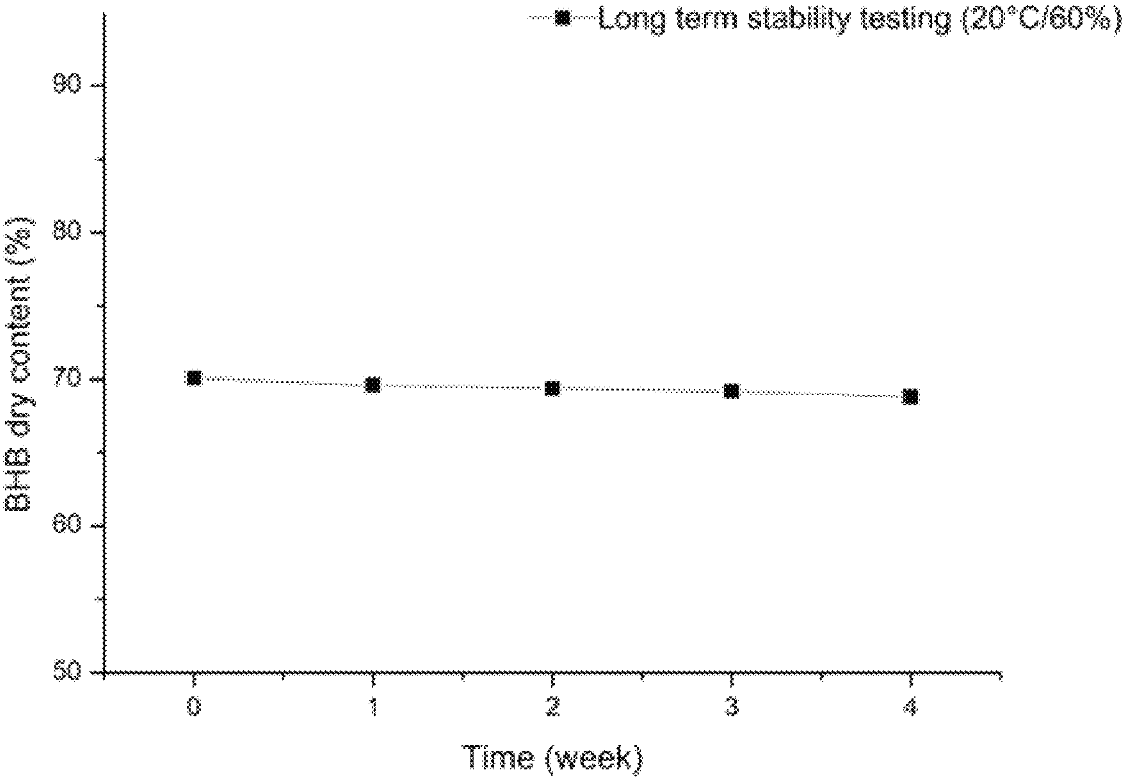
Figure 4G:
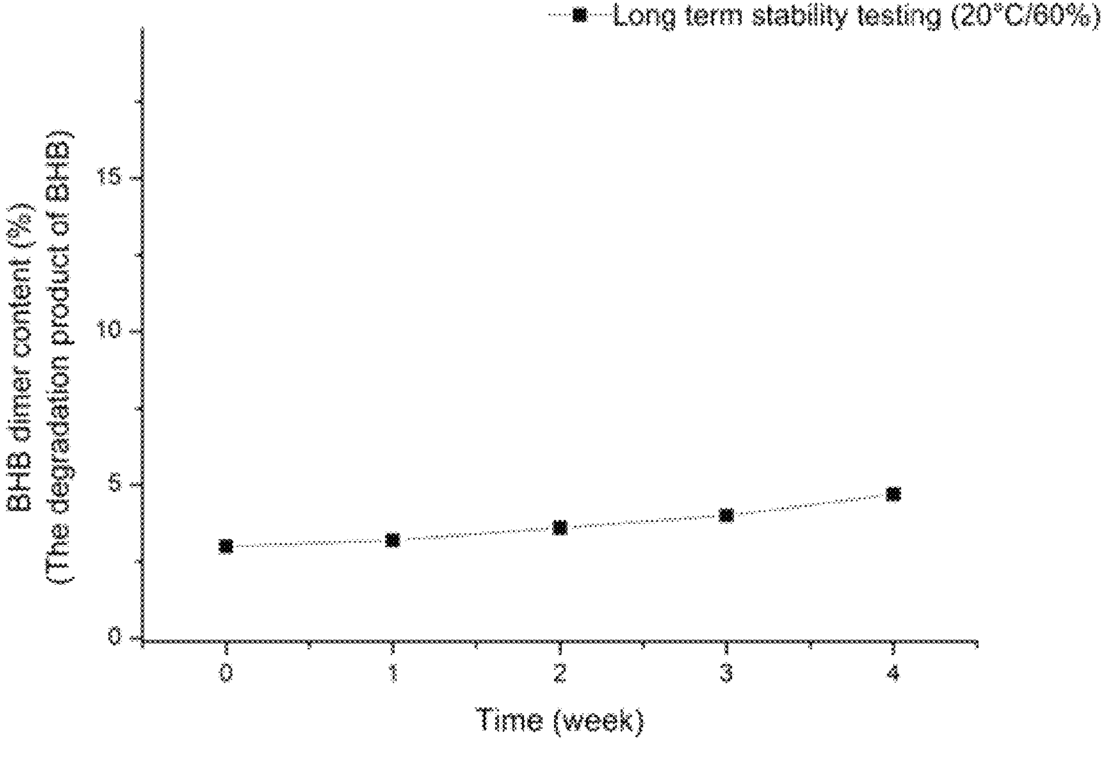

FIGS. 4A-4G show the stability of BHB liposome after long-term storage under conventional condition at 20° C. and 60% relative humidity. More specifically, FIG. 4A shows HPLC analysis of initial BHB liposome (week 0). FIG. 4B shows HPLC analysis results of BHB liposome after 1-week storage (20° C./60%). FIG. 4C shows HPLC analysis results of BHB liposome after 2-week storage (20° C./60%). FIG. 4D shows HPLC analysis results of BHB liposome after 3-week storage (20° C./60%). FIG. 4E shows HPLC analysis results of BHB liposome after 4-week storage. FIG. 4F shows BHB dry content (%) of BHB liposome stored under conventional condition. FIG. 4G shows BHB dimer content (%) of BHB liposome stored under conventional condition (BHB dimer indicates the degradation product of BHB).

As shown in FIGS. 3A-3G, after the long-term storage under cold condition (5° C.), there was no significant change in the contents of BHB liposomes. As shown in FIGS. 4A-4G, after long-term storage at 20° C. and 60% relative humidity, the BHB dry content decreased slightly from 70.1% to 68.8%, and the impurity (as indicated by BHB dimers) increased slightly from 3.0% to 4.7%, both of which are within the acceptable range. Accordingly, stability analysis showed that the BHB liposomes of the present invention demonstrate great stability.

Example 10 Effects of BHB Acid and BHB Liposomes on Blood Ketone Levels

The ketogenic potential of BHB Acid and BHB Liposome was analyzed according to Csilla's method with slight modifications (Nutrients. 2019 October; 11(10): 2330).

Specific Pathogen Free (SPF) male Institute of Cancer Research (ICR) mice were purchased from Qinglongshan Animal Breeding Center. All mice were on standard diet, and housed individually in a steel cage under standard photoperiod (12:12 h light-dark cycle) in a room at 24° C., and tap water was freely available. Prior to treatments, the mice fasted for 16 hours.

For treatments, a number of 30 mice were randomly divided into three groups—control group, BHB group, and BHB liposome group. The mice were treated via oral gavage at 0.1 ml/10 g body weight as shown in Table 9. The BHB group mice were treated with free acid form of R-BHB in water (once daily) at 9.92 mmol/kg, the BHB liposome group mice were treated with liposomal R-BHB free acid in water (once daily) at 9.92 mmol/kg, and the control group mice were treated with water. The pH of the administrated treatment solutions or water were all adjusted to 7 before administration. And the blood ketone levels were measured using a blood ketone meter at 0, 10, 20, 30, 45, 60, 90, 120, and 240 min after administration.

TABLE 9

| Treatment Plan | | | | |
|---|---|---|---|---|
| Group | Dose (mg/kg body weight) | BHB content (w/w) | Dose (mmol/kg body weight) | Gavage volume |
| Control | / | / | / | 0.1 mL/10 g |
| BHB | 1860.7 mg/kg | 55.5% | 9.92 mmol/kg | 0.1 mL/10 g |
| BHB liposomes | 1516.4 mg/kg | 68.1% | 9.92 mmol/kg | 0.1 mL/10 g |

Figure 5:
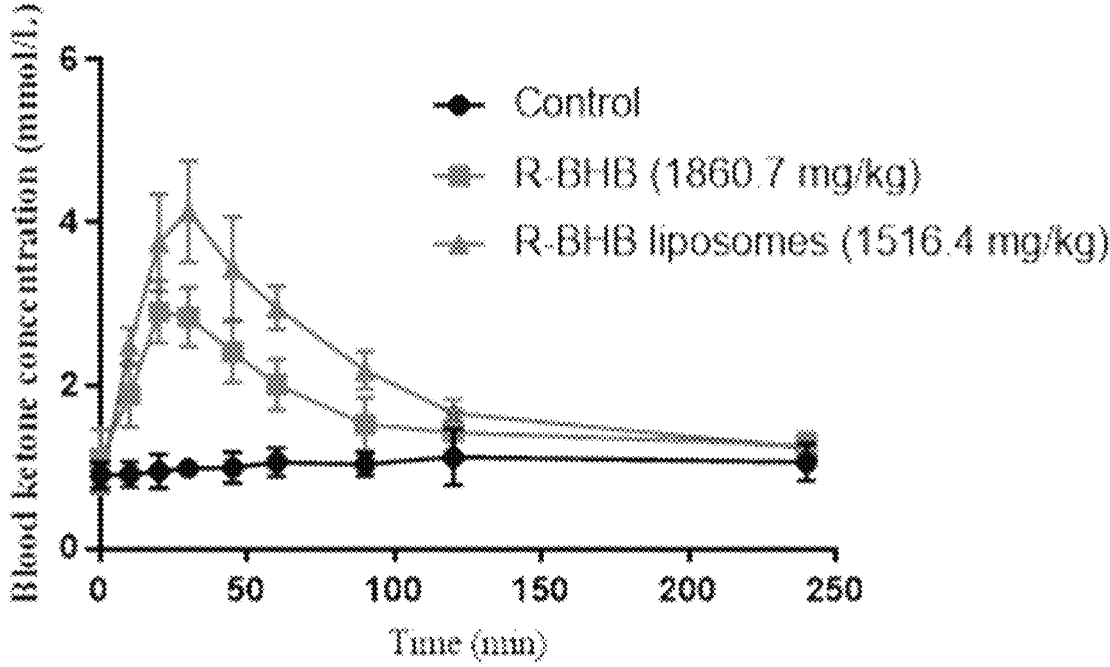
FIG. 5 shows blood ketone levels at different time points after oral administration of BHB free acid or BHB liposome respectively.

FIG. 5 shows blood ketone levels at different time points after oral administration of BHB acid or BHB liposome as shown in Table 9. The highest blood ketone level is 2.8 mmol/L for BHB acid treatment group and 4.1 mmol/L for BHB liposome treatment group. The highest blood ketone level of R-BHB liposome was 1.41 times of that of R-BHB free acid. And the area under the curve of R-BHB liposome is 1.25 times that of R-BHB free acid, thus, the bioavailability of BHB liposome is significantly higher than that of R-BHB. In conclusion, BHB liposome demonstrated higher ketogenic potential, better bioavailability, and achieved better nutritional ketosis as compared to BHB free acid.

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

What is claimed is:

1. A liposome comprising an active ingredient and one 1, membrane, or one inner membrane and one outer membrane, wherein the one membrane or each of the inner and outer membranes defines an interior space within the one membrane or the inner membrane, and/or between the inner and outer membranes, each membrane comprises a plurality of lipid molecules, and the active ingredient is entrapped inside the interior space or embodied in the membrane or membranes;

wherein the active ingredient comprises β-hydroxybutyrate acid (BHB), a physiologically acceptable salt, ester, or mixture thereof;

the liposome has a reverse vesicle structure, composed of a bilayer with the hydrophilic head groups facing the inside of the bilayer surrounding a nonpolar core with the hydrophobic tails facing both the core and the exterior of the liposome, and the active ingredient is embodied in a lipid bilayer membrane and forms a part of the lipid bilayer membrane;

wherein the active ingredient has a mass percentage ranging from 1% to 95% of the liposome's total mass;

wherein the lipid molecules include phospholipid and has a mass percentage from 1% to 40% of the liposome's total mass;

and wherein the liposome further comprises: a co-emulsifier has a mass percentage ranging from 1% to 40% of the liposome's total mass;

a stabilizer has a mass percentage ranging from 1% to 40% of the liposome's total mass; and water has a mass percentage ranging from 0.01% to 10% of the liposome's total mass.

2. The liposome of claim 1, wherein the active ingredient is free acid form of BHB.

3. The liposome of claim 1, wherein the BHB, physiologically acceptable salt, or ester thereof is a mixture of R- and S-enantiomers.

4. The liposome of claim 1, wherein the active ingredient further comprises one or more additional hydrophilic components.

5. The liposome of claim 1, wherein the phospholipid comprises phosphatidylcholine, phosphatidylethanolamine, phosphatidylserine, phosphatidylinositol, lysophosphatidylcholine, lysophosphatidylethanolamine, dipalmitoyl phosphatidylcholine, dioleoyl phosphatidylcholine, dilinoleoyl phosphatidylcholine, distearoyl phosphatidylcholine, or a combination thereof.

6. The liposome of claim 1, wherein the co-emulsifier comprises polyethylene glycol 200-2000, glycerol, sorbitol, or a combination thereof.

7. The liposome of claim 1, wherein the stabilizer comprises medium-chain fatty acid glyceride, soybean oil, sunflower oil, or a combination thereof.

8. The liposome of claim 1, wherein the BHB, physiologically acceptable salt, or ester thereof is an R-enantiomer or an S-enantiomer.

9. A method for increasing or sustaining blood ketone level in a subject in need thereof, comprising administrating to the subject the BHB liposome of claim 1.

* * * * *